United States Patent [19]

Nishimura et al.

[11] Patent Number: 5,440,047

[45] Date of Patent: Aug. 8, 1995

[54] METHOD OF PREPARING 2-CHLORO-PYRIDINEMETHANOL

[75] Inventors: Yasunobu Nishimura; Akihiro Ishii; Yuzuru Morino; Yoshiyuki Kikuchi, all of Kawagoe, Japan

[73] Assignee: Central Glass Company, Limited, Yamaguchi, Japan

[21] Appl. No.: 252,484

[22] Filed: Jun. 1, 1994

[30] Foreign Application Priority Data

Jun. 2, 1993 [JP] Japan .................. 5-132021

[51] Int. Cl.⁶ .......................... C07D 213/30
[52] U.S. Cl. .................................. 546/344
[58] Field of Search .............. 546/341, 344, 345

[56] References Cited

U.S. PATENT DOCUMENTS 4,576,629  3/1986  Morland et al. ................ 71/90
5,324,841  6/1994  Nishimura ..................... 546/345

FOREIGN PATENT DOCUMENTS 58-170779  10/1983  Japan .
61-12682   1/1986   Japan .
1-230556   9/1989   Japan .
4-243867   8/1992   Japan .
5-230025   9/1993   Japan .

OTHER PUBLICATIONS

March, J. Advanced Organic Chemistry. Reactions, Mechanisms and Structure: McGraw Hill. 1977. P. 367.
Liotta, C. L., Harris, H. P., McDermott, M., Gonzalez, T., and Smith, K. Chemistry of "Naked" Anions II. Reactions of the 18-Crown-6 Complex of Potassium Acetate with Organic Substrates in Aprotic Organic Solvents. Tetrahedron Letters 28, 2417, 1974.
Hamana, et al., *UDC* 547.821.07, vol. 81, "Studies on Tertiary Amine Oxide. IX. Reactions of 2-Substituted Pyridine 1-Oxides with Acetic Anhydride", pp. 574-578. (1961).
Chemical Abstracts, vol. 55, No. 24, 1961, Abstract No. 24743f.
Barnes, et al., Tetrahedron, vol. 38, No. 22, 1982, Oxford GB, pp. 3277-3280, "The Preparation of 4-and 6-Chloro-2 Chloromethylpyridine".

*Primary Examiner*—C. Warren Ivy
*Assistant Examiner*—Evelyn Huang
*Attorney, Agent, or Firm*—Keck, Mahin & Cate

[57] ABSTRACT

The invention relates to a method of preparing 2-chloro-pyridinemethanol represented by the following formula (1). The method includes the steps of: (a) reacting 2-chloro-monochloromethylpyridine with an alkali metal salt of a carboxylic acid and/or a hydrate of the alkali metal salt so as to form an ester derivative; and (b) hydrolyzing the ester derivative so as to form the 2-chloro-pyridinemethanol.

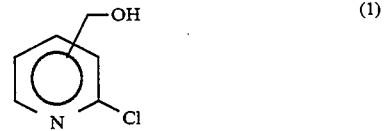

(1)

10 Claims, No Drawings

METHOD OF PREPARING 2-CHLORO-PYRIDINEMETHANOL

BACKGROUND OF THE INVENTION

The present invention relates to a method of preparing 2-chloro-pyridinemethanol which is represented by the following formula (1) and is useful as a raw material of medicines and agricultural chemicals.

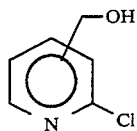
(1)

For example, 2-chloro-pyridinemethanol represented by the formula (1) is known as an intermediate for preparing an anti-peptic ulcer agent (see JP-A-58-170779 and JP-A-1-230556) and as an intermediate for preparing an insecticide (see JP-A-61-12682 ).

Hitherto, there have been some proposed methods of preparing 2-chloro-pyridinemethanol represented by the formula (1). Of these, for example, there is provided a method in which 2-chloro-pyridinemethanol is produced by reducing 2-chloro-(iso)nicotinic acid or its ester with sodium boron hydride (see JP-A-1-230556 and U.S. Pat. No. 4,576,629). However, this method has a problem that diborane and hydrogen which have the risk of explosion are produced. There is provided another method in which 2-chloro-4-pyridinemethanol is produced by hydrogenating 2-chloro-4-cyanopyridine in the presence of a catalyst for hydrogenolysis (see JP-A-4-243867). However, this method has problems that a large amount of 2-chloro-4-aminomethylpyridine as a by-product is produced and that chlorine of the pyridine nucleus is released in the reaction. There is provided still another method in which 2-chloro-4-methylpyridine-N-oxide is reacted with acetic anhydride so as to form 2-chloro-4-acetoxymethylpyridine and then this acetoxymethylpyridine is hydrolyzed so as to form 2-chloro-pyridinemethanol (see Hamana et al. (Journal of the Pharmaceutical Society of Japan written in Japanese) Vol. 81, pp. 574–578 (1961), cf. Chemical Abstracts, vol. 55, no. 24, 2473f, (1961). However, this method has a problem that a large amount of by-product in the form of tar is produced by the reaction between 2-chloro-4-methyl-pyridine-N-oxide and acetic anhydride.

SUMMARY OF THE INVENTION

It is therefore an object of the present invention to provide an improved method of preparing 2-chloro-pyridinemethanol, which is free of the above-mentioned drawbacks.

According to the present invention, there is provided a method of preparing 2-chloro-pyridinemethanol represented by the following formula (1),

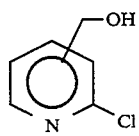
(1)

the method comprising the steps of:

(a) reacting 2-chloro-monochloromethylpyridine represented by the following formula (2) with an alkali metal salt of a carboxylic acid represented by the following formula (3) and/or a hydrate of said alkali metal salt so as to form an ester derivative represented by the following formula (4); and (b) hydrolyzing said ester derivative so as to form said 2-chloro-pyridinemethanol,

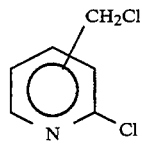
(2)

(3)

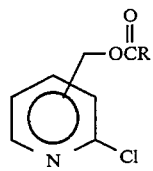
(4)

wherein R is hydrogen, alkyl group, alkenyl group, phenyl group or substituted phenyl group, and M is alkali metal.

By virtue of a method according to the present invention, 2-chloro-pyridinemethanol represented by the formula (1) can be produced easily, effectively and quantitatively.

DESCRIPTION OF THE PREFERRED EMBODIMENTS

An improved method of preparing 2-chloro-pyridinemethanol according to the present invention will be described in the following. The method comprises first and second reactions.

In the first reaction, 2-chloro-monochloromethylpyridine represented by the above formula (2) is reacted with an alkali metal salt of carboxylic acid represented by the above formula (3) and/or a hydrate of the alkali metal salt so as to form an ester derivative represented by the above formula (4). In the second reaction, the ester derivative is hydrolyzed so as to produce the 2-chloro-pyridinemethanol.

A raw material of the first reaction, 2-chloro-monochloromethylpyridine represented by the above formula (2), can be easily produced by a method shown in JP-A-5-230025 and the corresponding U.S. Pat. No. 5,324,841, the disclosure of which is hereby incorporated by reference.

In this method, a side-chain methyl group of 2-chloro-methylpyridine is chlorinated while hydrogen chloride and/or hydrochloride of the 2-chlormethylpyridine which are formed in the reaction are neutralized with a basic aqueous solution. The reaction of this method is a successive reaction which is similar to chlorination of a side-chain methyl group of toluene. Therefore, the reaction product by this method is a mixture containing 2-chloro-methylpyridine which is a non-chlorinated raw material, 2-chloro-monochloromethylpyridine, 2-chloro-dichloromethylpyridine and/or 2-chloro-trichloromethylpyridine.

According to the present invention, when this mixture is used as a raw material of the first reaction, methyl group, dichloromethyl group, trichloromethyl group and chlorine of pyridine nucleus, which are contained in the mixture, are stable in the first and second reactions. Only monochloromethyl group is, however, selectively esterified in the first reaction to produce the ester derivative, and then only the ester derivative is selectively hydrolyzed in the second reaction to produce the 2-chloro-pyridinemethanol. Therefore, when the mixture is used as a raw material of the first reaction, it is not necessary to purify the same before the first reaction. Furthermore, the unpurified reaction product of the first reaction can be used in the second reaction. It is needless to say that purified 2-chloro-monochloromethylpyridine can be used as a raw material of the first reaction.

In case that the above mixture is used as a raw material of the first reaction, 2-chloro-methylpyridine which is a non-chlorinated raw material can be easily recovered with a high purity through distillation or the like after the production of the ester derivative and/or after the production of 2-chloro-pyridinemethanol. Therefore, the objective 2-chloro-pyridinemethanol can be effectively obtained by reusing the recovered 2-chloro-methylpyridine as a raw material of the chlorination.

In case that the mixture is used as a raw material of the first reaction, it is preferable that the chlorination of side-chain methyl group of 2-chloro-methylpyridine is limited to a lower order. That is, it is preferable that the production of 2-chloro-dichloromethylpyridine and 2-chloro-trichloromethyl-pyridine in the chlorination is suppressed as much as possible, and that a large amount of the objective 2-chloro-monochloromethylpyridine is produced.

A raw material of the first reaction, 2-chloro-monochloromethylpyridine represented by the formula (2), represents 2-chloro-3-monochloromethyl-pyridine, 2-chloro-4-monochloromethylpyridine, 2-chloro-5-monochloromethylpyridine and 2-chloro-6-monochloromethyl-pyridine. A raw material of the chlorination, 2-chloro-methylpyridine, represents 2-chloro-3-methylpyridine, 2-chloro-4-methylpyridine, 2-chloro-5-methylpyridine and 2-chloro-6-methylpyridine.

Examples of an alkali metal of the alkali metal salt and its hydrate are sodium and potassium. Examples of an carboxylic acid of the alkali metal salt and its hydrate are formic acid, acetic acid, propionic acid, butyric acid, acrylic acid, benzoic acid and substituted benzoic acid. However, in view of easiness of hydrolysis of the ester derivative, it is preferable to use sodium formate, potassium formate, sodium acetate, sodium acetate trihydrate or potassium acetate. If one of these is used, the obtained ester derivative is easily hydrolyzed in the second reaction.

The first reaction can proceed by only mixing 2-chloro-monochloromethylpyridine represented by the formula (2) and the alkali metal salt of carboxylic acid and/or its hydrate. If the first reaction is conducted in a non-protonic polar solvent such as acetonitrile, the first reaction proceeds smoothly by only mixing the above-mentioned two compounds. However, in this case, it is necessary to distill off the solvent upon a post-treatment after the first reaction. Therefore, it is preferable to conduct the first reaction without using any solvent or in a solvent which is immiscible with water. In this case, it is necessary to add a phase transfer catalyst to proceed the first reaction smoothly.

Examples of the solvent which is immiscible with water are aromatic hydrocarbons such as benzene, toluene and xylene, aliphatic hydrocarbons such as hexane and cyclohexane, esters such as ethyl acetate and butyl acetate and ethers such as dibutyl ether. Examples of the phase transfer catalyst are quaternary ammonium salts such as tetrabutylammonium bromide and tetrabutylammonium hydrogensulfate, quaternary phosphonium salts such as tetraphenylphosphonium chloride and ethyltriphenylphosphonium bromide, crown ethers such as 18-crown-6-ether and polyethers such as polyethylene glycol. The amount of phase transfer catalyst is adjusted depending on the type of the catalyst and the desired reaction rate. However, it is usual that the phase transfer catalyst amounts to 0.001 to 20 wt % based on the weight of the alkali metal salt. If it is less than 0.001 wt %, the reaction rate becomes too slow. Even if more than 20 wt % is used, the reaction rate does not increase significantly. Thus, adding more than 20 wt % is uneconomical. It is more preferable that the phase transfer catalyst amounts to 0.01 to 10 wt % based on the weight of the alkali metal salt.

The first reaction is an exothermic reaction and proceeds smoothly at a temperature ranging from room temperature to 150° C. If it is lower than room temperature, the reaction rate becomes too slow. If it is higher than 150° C., the yield becomes too low due to decomposition. It is more preferable to conduct the first reaction at a temperature ranging from 40° to 130° C.

The ester derivative obtained by the first reaction may be subjected to a conventional post-treatment, then isolated through distillation under reduced pressure, and then hydrolyzed in the second reaction. However, as is mentioned hereinabove, the ester derivative obtained by the first reaction may be directly hydrolyzed in the second reaction without having the post-treatment and the isolation.

In case that the mixture obtained by the chlorination is used as a raw material of the first reaction, as an example, the reaction product of the first reaction may be purified by distilling off impurities such as 2-chloro-methylpyridine and 2-chloro-dichloromethylpyridine which have low boiling points, and then the distillation residue is hydrolyzed in the second reaction. In this case, 2-chloro-methylpyridine which has been distilled off can be recovered and then reused as a raw material of the chlorination. In case that the mixture obtained by the chlorination is used as a raw material of the first reaction, as another example, the reaction product of the first reaction may be directly used in the second reaction without having the purification. In this case, 2-chloro-methylpyridine is recovered after the second reaction and then reused as a raw material of the chlorination.

The ester derivative represented by the formula (4) is easily hydrolyzed in the second reaction by a conventional method. In fact, the ester derivative is easily hydrolyzed by an acid or a base to the objective 2-chloro-pyridinemethanol represented by the formula (1).

Examples of the acid are mineral acids such as hydrochloric acid, hydrobromic acid, sulfuric acid and phosphoric acid and aqueous solutions of these. Examples of the base are aqueous solutions of sodium hydroxide and potassium hydroxide. When an alcohol solution of the base is used, it is possible that chlorine atom of the pyridine nucleus is replaced by the alcohol. Therefore, it is not preferable to use an alcohol solution of the base.

It suffices to add the acid or the base in the amount of at least one equivalent to one equivalent of the ester derivative. It is preferable that the amount of the acid or the base is from one to five equivalents. Adding more than five equivalents is not an obstacle to the second reaction, but is uneconomical. It is more preferable that the amount is from one to two equivalents.

The second reaction proceeds smoothly at a temperature ranging from room temperature to 120° C. by using either the acid or the base. If it is lower than room temperature, the reaction rate becomes too slow. If it is higher than 120° C., the yield becomes too low due to the decomposition. It is more preferable that the reaction temperature of the second reaction is from 40° to 100° C.

2-chloro-pyridinemethanol obtained by the second reaction can be subjected to a conventional post-treatment, and then isolated by distillation under reduced pressure or by recrystallization. As is mentioned hereinabove, in case that the mixture obtained by the chlorination is used as a raw material of the first reaction, 2-chloro-methylpyridine may be distilled off and isolated after the second reaction to be reused as a raw material in the chlorination.

For example, when the ester derivative having a relatively high purity is hydrolyzed by the acid aqueous solution in the second reaction, impurities such as 2-chloro-methylpyridine and 2-chloro-dichloromethylpyridine are selectively removed from an aqueous reaction solution containing 2-chloro-pyridinemethanol acid salt to an organic solvent phase by washing the aqueous reaction solution with an organic solvent such as methylene chloride. Then, the aqueous reaction solution is made basic by neutralization, and then 2-chloropyridinemethanol having a high purity is isolated through solvent extraction.

The present invention will be illustrated with the following nonlimitative examples.

EXAMPLE 1

A. Chlorination of a Side Chain Methyl Group of 2-chloro-4-methylpyridine

First, 200 g (1.569 mol) of 2-chloro-4-methylpyridine was mixed with 200 g of water in a reaction vessel. The mixture was stirred and liquid temperature was raised up to 65° C. After that, 2.0 g of 2,2'-azobisisobutyronitrile (AIBN) was added to the mixture. 10 min after the addition of AIBN, the chlorine gas bubbling into the mixture was started at a rate of 26 g/hr, and liquid temperature was maintained at a temperature ranging from 68° to 72° C. during the bubbling. 8 min after the initiation of the bubbling, induction period of chlorination appeared. 30 min after the initiation of bubbling, a continuous dropping of 25% potassium carbonate aqueous solution was began at a rate of 76.2 g/hr. During the dropping, pH value of the reaction liquid was maintained within a range from 1 to 2. After the completion of chlorination, the reaction liquid was cooled down. Then, 130 g of 25% potassium carbonate was dropped into the reaction liquid so as to make the same basic. Then, oil as the reaction product was recovered by a conventional solvent extraction method. The yield was 234.4 g. By the analysis with a gas chromatograph, it was found that the reaction product contained 47.44% of 2-chloro-4-methylpyridine which is a non-chlorinated raw material, 45.38% of 2-chloro-4-monochloromethylpyridine and 5.71% of 2-chloro-4-dichloromethylpyridine.

B. Production of 2-chloro-4-acetoxymethylpyridine

First, 234.4 g of the reaction product of Step A (chlorination) was mixed with 76.9 g (0.783 mol) of anhydrous potassium acetate and 2.0 g of tetrabutylammonium hydrogensulfate in a reaction vessel. Then, the mixture was stirred for 4 hr while the liquid temperature was maintained at 80° C. After that, the reaction liquid was cooled down. By the analysis with a gas chromatograph, it was found that the obtained organic matter as the intermediate product contained 48.86% of 2-chloro-4-methylpyridine, 0.66% of 2-chloro-4-monochloromethylpyridine, 4.97% of 2-chloro-4-dichloromethylpyridine and 44.00% of 2-chloro-4-acetoxymethylpyridine.

C. Production of 2-chloro-4-pyridinemethanol

First, 380 g of 15% NaOH aqueous solution was added to the above-mentioned intermediate product in a reaction vessel. Then, the reaction mixture was stirred for 2 hr at a temperature of 60° C. After the reaction mixture was cooled down, 200 g of water was added thereto. Then, the reaction product was extracted two times from the reaction mixture with methylene chloride. The extract was washed with water and a saturated salt solution and then dried. Then, methylene chloride was distilled off. With this, oil was recovered. This recovered oil was distilled under reduced pressure. With this, 2-chloro-4-methylpyridine which is a nonchlorinated raw material and 2-chloro-4-pyridinemethanol as the objective reaction product were recovered. The recovered 2-chloro-4-methylpyridine had a yield of 79.5 g, a boiling point under 15 mmHg of from 86° to 87° C., and a purity (GC purity) of 98.35%. The recovered 2-chloro-4-pyridinemethanol had a yield of 76.6 g, a boiling point under 1 mmHg of from 108° to 110° C., and a purity (GC purity) of 98.60%.

EXAMPLE 2

A. Chlorination of a Side Chain Methyl Group of 2-chloro-4-methylpyridine

Step A (chlorination) of Example 1 was repeated. With this, oil as the reaction product was recovered. By the analysis with a gas chromatograph, it was found that the reaction product contained 53.07% of 2-chloro-4-methylpyridine which is a non-chlorinated raw material, 40.84% of 2-chloro-4-monochloromethylpyridine and 4.56% of 2-chloro-4-dichloromethylpyridine.

B. Production of 2-chloro-4-acetoxymethylpyridine

First, the reaction product of Step A was mixed with 69.17 g (0.705 mol) of anhydrous potassium acetate in a reaction vessel. Then, the mixture was stirred for 2 hr while the liquid temperature was maintained at 80° C. After that, the mixture was analyzed with a gas chromatograph. With this, it was found that the reaction product of Step A did not change in chemical composition. Then, 1.0 g of tetrabutylammonium hydrogensulfate was added to the mixture, and then stirring was conducted for 7 hr at a temperature of 80° C. It was confirmed that an exothermic reaction has occurred. By the analysis with a gas chromatograph, it was found that the obtained organic matter as the intermediate product contained 47.89% of 2-chloro-4-methylpyridine, 0.58% of 2-chloro-4-monochloromethylpyridine, 3.97% of 2-chloro-4-dichloromethylpyridine and 45.19% of 2-chloro-4-acetoxymethylpyridine.

C. Production of 2-chloro-4-pyridinemethanol

First, 342 g of 15% NaOH aqueous solution was added to the above-mentioned intermediate product in a reaction vessel. Then, the reaction mixture was stirred for 1 hr at a temperature of 70° C. After the reaction mixture was cooled down, 200 g of water was added thereto. Then, oil was recovered by the same solvent extraction method as that of Step C of Example 1. This recovered oil was distilled under reduced pressure. With this, 93 g of a distillate having a boiling point of from 85° to 89° C. under 15 mmHg was obtained. 2-chloro-4-methylpyridine was recovered from this distillate. The recovered 2-chloro-4methylpyridine had a yield of 85.2 g, a boiling point of from 86° to 87° C. under 15 mmHg, and a purity (GC purity) of 98.56%. The distillation residue was recrystallized using 320 g of 1,2-dichloroethane. With this, 2-chloro-4-pyridinemethanol crystals were obtained. The obtained 2-chloro-4-pyridinemethanol had a yield of 52.6 g, a melting point of from 66.1° to 66.4° C., and a purity (GC purity) of 99.34%.

EXAMPLE 3

A. Chlorination of a Side Chain Methyl Group of 2-chloro-4-methylpyridine

Step A (chlorination) of Example 1 was repeated. With this, oil as the reaction product was recovered. By the analysis with a gas chromatograph, it was found that the reaction product contained 51.61% of 2-chloro-4-methylpyridine which is a non-chlorinated raw material, 42.40% of 2-chloro-4-monochloromethylpyridine and 4.56% of 2-chloro-4-dichloromethylpyridine.

B. Production of 2-chloro-4-acetoxymethylpyridine

In this step, 2-chloro-4-acetoxymethylpyridine was isolated from a reaction mixture.

First, the reaction product of Step A (chlorination) was mixed with 71.8 g (0.732 mot) of anhydrous potassium acetate and 2.0 g of tetrabutylammonium hydrogensulfate in a reaction vessel. Then, the reaction mixture was stirred for 4 hr while the liquid temperature was maintained at 80° C. After the reaction mixture was cooled down, 300 g of water was added to the reaction mixture. Then, the reaction product was extracted two times from the reaction mixture with methylene chloride. The extract was washed with water and a saturated salt solution and then dried. By the analysis with a gas chromatograph, the obtained organic matter contained 48.15% of 2-chloro-4-methylpyridine, 0.08% of 2-chloro-4-monochloromethylpyridine, 4.14% of 2-chloro-4-dichloromethylpyridine and 45.99% of 2-chloro-4-acetoxymethylpyridine. Then, 2-chloro-4-methylpyridine and 2-chloro-4-acetoxymethylpyridine were recovered from the organic matter by distillation under reduced pressure. The recovered 2-chloro-4-methylpyridine had a yield of 95.11 g, a boiling point of from 86° to 87° C. under 15 mmHg, and a purity (GC purity) of 98.51%. The recovered 2-chloro-4-acetoxymethylpyridine had a yield of 119.12 g, a boiling point of from 95° to 100° C. under 1 mmHg, and a purity (GC purity) of 91.34%.

C. Production of 2-chloro-4-pyridinemethanol

First, 92.75 g of 2-chloro-4-acetoxymethylpyridine recovered in Step B was mixed with 104.3 g of water and 104.3 g of concentrated hydrochloric acid. This 2-chloro-4-acetoxymethylpyridine having a purity of 91.34% contained 7.09% of 2-chloro-4-dichloromethylpyridine. The reaction mixture was stirred for 3 hr at a temperature of 50° C. After the reaction mixture was cooled down, the reaction mixture was washed two times with 25 ml of methylene chloride. With this, impurities such as 2-chloro-4-dichloromethylpyridine were removed. Then, the reaction mixture was made basic by adding thereto 276 g of 50% $K_2CO_3$ aqueous solution. Then, the reaction product was extracted two times from the reaction mixture with 250 ml of methylene chloride. Then, the extract was washed with water and a saturated salt solution and then dried. Then, extraction solvent was distilled off. With this, 2-chloro-4-pyridinemethanol in the form of colorless solid was obtained. This 2-chloro-4-pyridinemethanol had a yield of 62.0 g, a melting point of from 66.1° to 66.5° C., and a purity (GC purity) of 99.34%.

EXAMPLE 4

A. Chlorination of a Side Chain Methyl Group of 2-chloro-4-methylpyridine

Step A (chlorination) of Example 1 was repeated. After completion of the chlorination, the reaction mixture was cooled down. Then, the reaction mixture was made basic by adding thereto 25% potassium carbonate aqueous solution. Then, the reaction product was extracted from the reaction mixture with 400 g of ethyl acetate. The extract was washed with water and a saturated salt solution, and then dried. By the analysis with a gas chromatograph, the recovered ethyl acetate solution contained 50.70% of 2-chloro-4-methylpyridine, 42.78% of 2-chloro-4-monochloromethylpyridine and 5.21% of 2-chloro-4-dichloromethylpyridine.

B. Production of 2-chloro-4-acetoxymethylpyridine

The ethyl acetate solution recovered in the Step A was mixed with 134.4 g (0.988 mol) of sodium acetate trihydrate and 5.0 g of tetrabutylammonium hydrogensulfate. The reaction mixture was stirred for 13.5 hr at a temperature of 90° C. By the analysis with a gas chromatograph, the obtained organic matter contained 48.87% of 2-chloro-4-methylpyridine, 0.78% of 2-chloro-4-monochloromethylpyridine, 4.72% of 2-chloro-4-dichloromethylpyridine and 42.90% of 2-chloro-4-acetoxymethylpyridine.

EXAMPLE 5

Production of 2-chloro-4-acetoxymethylpyridine

First, 0.5 g of an organic matter containing 4.14% of 2-chloro-4-methylpyridine, 91.35% of 2-chloro-4-monochloromethylpyridine and 4.17% of 2-chloro-4-dichloromethylpyridine was mixed with 0.36 g of anhydrous potassium acetate and 7 ml of acetonitrile. The reaction mixture was stirred for 5.5 hr at reflux temperature. By the analysis with a gas chromatograph, the obtained organic matter contained 3.09% of 2-chloro-4-methylpyridine, 0.49% of 2-chloro-4-monochloromethylpyridine, 3.51% of 2-chloro-4-dichloromethylpyridine and 92.62% of 2-chloro-4-acetoxymethylpyridine.

What is claimed is:

1. A method of preparing 2-chloro-pyridinemethanol represented by the following formula (1),

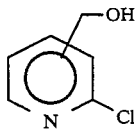

(1)

the method comprising the steps of:
(a) forming a reaction liquid comprising a 2-chloromethylpyridine and a chlorine radical so that hydrochloride of 2-chloro-methylpyridine and optionally hydrogen chloride are formed;
(b) controlling the pH of the reaction liquid of step (a) by the addition of a basic aqueous solution so that the pH of the reaction liquid falls within a range of 0.5 to 3.0 and that a reaction product including part of said 2-chloro-methylpyridine which was not chlorinated in step (a), 2-chloro-monochloromethylpyridine represented by the following formula (2), 2-chloro-dichloromethylpyridine and optionally 2-chloro-trichloromethylpyridine is formed;
(c) reacting the reaction product of step (b) with an alkali metal salt of a carboxylic acid represented by the following formula (3) and/or a hydrate of said alkali metal salt so to selectively esterify the monochloromethyl group of the 2-chloro-monochloromethylpyridine that a reaction product including said 2-chloro-methylpyridine, said 2-chloro-dichloromethylpyridine, and an ester derivative represented by the following formula (4) and optionally including said 2-chloro-monochloromethyl-pyridine which has not been esterified and 2-chloro-trichloromethylpyridine; and
(d) selectively hydrolyzing said ester derivative so as to form said 2-chloro-pyridinemethanol,

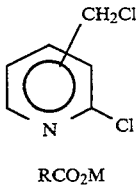

(2)

RCO$_2$M (3)

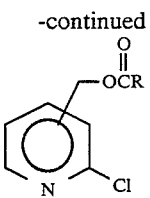

(4)

wherein R is hydrogen, alkyl group, alkenyl group, phenyl group or substituted phenyl group, and M is alkali metal.

2. A method according to claim 1, wherein said 2-chloro-monochloromethylpyridine is reacted with said alkali metal salt and/or said hydrate in the presence of a phase transfer catalyst without using any solvent or in a solvent which is immiscible with water.

3. A method according to claim 1, wherein said alkali metal salt and said hydrate are selected from the group consisting of sodium formate, potassium formate, sodium acetate, sodium acetate trihydrate and potassium acetate.

4. A method according to claim 2, wherein said phase transfer catalyst is selected from the group consisting of quaternary ammonium salts, quaternary phosphonium salts, crown ethers and polyethers.

5. A method according to claim 2, wherein the amount of said phase transfer catalyst is from 0.001 to 20 wt % based on said alkali metal salt.

6. A method according to claim 1, wherein the step (a) is conducted at a temperature from room temperature to 150° C.

7. A method according to claim 1, wherein said ester derivative is hydrolyzed by an acid aqueous solution or a base aqueous solution.

8. A method according to claim 1, wherein the step (b) is conducted at a temperature from room temperature to 120° C.

9. A method according to claim 1, wherein, in step (d), the reaction product of step (c) is reacted with an acid or a base so as to hydrolyze said ester derivative.

10. A method according to claim 1, wherein, in step (d), said ester derivative is isolated from the reaction product of step (c) and said isolated ester derivative is hydrolyzed so as to form said 2-chloro-pyridinemethanol.

* * * * *